United States Patent [19]
Harris

[11] Patent Number: 5,626,577
[45] Date of Patent: May 6, 1997

[54] MANUALLY EXTENDABLE ELECTROCAUTERY SURGICAL APPARATUS

[76] Inventor: George A. Harris, P.O. Box 9811, Washington, D.C. 20016

[21] Appl. No.: 578,205

[22] Filed: Dec. 29, 1995

Related U.S. Application Data

[63] Continuation-in-part of Ser. No. 202,637, Feb. 28, 1994, abandoned.

[51] Int. Cl.$^6$ ................................................. A61B 17/39
[52] U.S. Cl. ................................ 606/45; 606/41; 606/49
[58] Field of Search ........................ 606/37–42, 45–50

[56] References Cited

U.S. PATENT DOCUMENTS

| | | | |
|---|---|---|---|
| 3,870,047 | 3/1975 | Gonser | 606/37 |
| 5,035,695 | 7/1991 | Weber, Jr. et al. | 606/42 |
| 5,234,429 | 8/1993 | Goldhaber | 606/45 |
| 5,318,565 | 6/1994 | Kuriloff et al. | 606/45 |

Primary Examiner—Angela D. Sykes
Assistant Examiner—Michael Peffley
Attorney, Agent, or Firm—Rodger H. Flagg

[57] ABSTRACT

The manually extendable electrocautery surgical apparatus slidably receives an electrode housing apparatus within an elongated aperture within a main housing. The electrode housing is slidably received upon a conductive post which provides an electrical connection to the electrode housing from a remote electrical supply source. An insulating outer layer surrounds the electrode housing apparatus, and the insulating outer layer is slidably received within the cylindrical cavity in the main housing. The electrode is inserted into the distal end of the electrode housing, and the electrode housing is adjustably positioned in relation to the main housing, to obtain the desired length during surgery. The main housing includes at least one actuation member for selectively controlling the flow of current to the electrode housing. The electrical current may further be adjusted to perform cutting or coagulating routines.

20 Claims, 2 Drawing Sheets

MANUALLY EXTENDABLE ELECTROCAUTERY SURGICAL APPARATUS

This patent application is a continuation-in-part of U.S. patent application Ser. No. 08/202,637 filed Feb. 28, 1994 (now abandoned) by George A. Harris, and the prior patent application is incorporated by reference herein.

BACKGROUND OF THE INVENTION

1. Field of the Invention

This invention relates to electrocautery surgical instruments and more particularly to an electrocautery scalpel system having an extendable electrode housing element to facilitate use in a variety of surgical locations without changing the electrode housing element.

2. Description of the Related Art

In general, electrocautery surgical instruments rely on the delivery of particular high current and high frequency electrical signals from a remote generator to selectively sever, clamp or coagulate living tissue during surgical procedures. The instruments deliver signals from an electrode extending from the distal end of the instrument. Surgery requires the delivery of the signals to a variety of locations within the body, thereby necessitating electrodes and their subsequent housing to be of a variety of sizes.

In use, the surgeon either exchanges one instrument with a particular size housing for a second instrument with a longer or shorter housing, or manually exchanges the electrode housing. This action is required by existing electrocautery surgical instruments, which distracts the surgeon from the patient and has given rise to the need for an electrocautery surgical instrument with an adjustably positioned electrode housing.

U.S. Pat. No. 5,025,695 issued to Weber, Jr. et al., on Jul. 30, 1991, discloses an extendable electrocautery surgical apparatus that delivers both electrode and suction capability. By manually manipulating a slidable element, the user can control the length of an electrode protruding out of a distal end of the unit. The Weber apparatus differs from this invention, in that the manual extension controls the extension of only the electrode, and therefore has a range of use limited to the size of the electrode selected. To expand the range of use of the Weber apparatus, it is necessary to exchange the electrode. The electrode may currently be purchased in a range of sizes.

U.S. Pat. No. 5,234,429 issued to Neil Goldhaber on Aug. 10, 1993 discloses a surgical cauterization instrument having a plurality of telescoping tubes, each tube having an outwardly projecting flange, and a flexible wire connecting a source of electrical voltage to an electrode positioned at the distal end of the telescoping tubes.

In contrast, this invention provides an extendable electrocautery surgical apparatus wherein the range of use is not limited to the size of the electrode, eliminating the need to purchase a electrode housing unit sizes.

SUMMARY OF THE INVENTION

Accordingly, it is an object of the present invention to provide an electrocautery surgical apparatus with an extendable electrode housing.

It is another object of the present invention to provide an electrocautery surgical apparatus that can accommodate electrodes of various sizes within the extendable electrode housing.

It is another object of the present invention to provide an electrocautery surgical apparatus that can selectively deliver electrical current and wave forms to an electrode that are sufficient to either cut or coagulate tissue which is brought into contact with the electrode.

To achieve the above and further objects, the present invention slidably receives an electrode housing apparatus within a cylindrical cavity within a main housing. The electrode housing is slidably received upon a conductive post which provides an electrical connection to the electrode housing from a remote electrical supply source, such as a commercially available generator. An insulating outer layer surrounds the electrode housing apparatus, and the insulating outer layer is slidably received within the cylindrical cavity in the main housing. The electrode is inserted into the distal end of the electrode housing, and the electrode housing is adjustably positioned in relation to the main housing, to obtain the desired length during surgery. The main housing includes at least one actuation means for selectively controlling the flow of current to the electrode housing. The electrical current may further be adjusted by the remote electric generator to selectively perform cutting or coagulating routines.

BRIEF DESCRIPTION OF THE DRAWINGS

The above mentioned and other features and objects of this invention and the manner of attaining them will become more apparent and the invention itself will be best understood by reference to the following description of the invention, when considered in conjunction with the accompanying drawings, wherein.

DETAILED DESCRIPTION OF THE DRAWINGS

Figure 1:
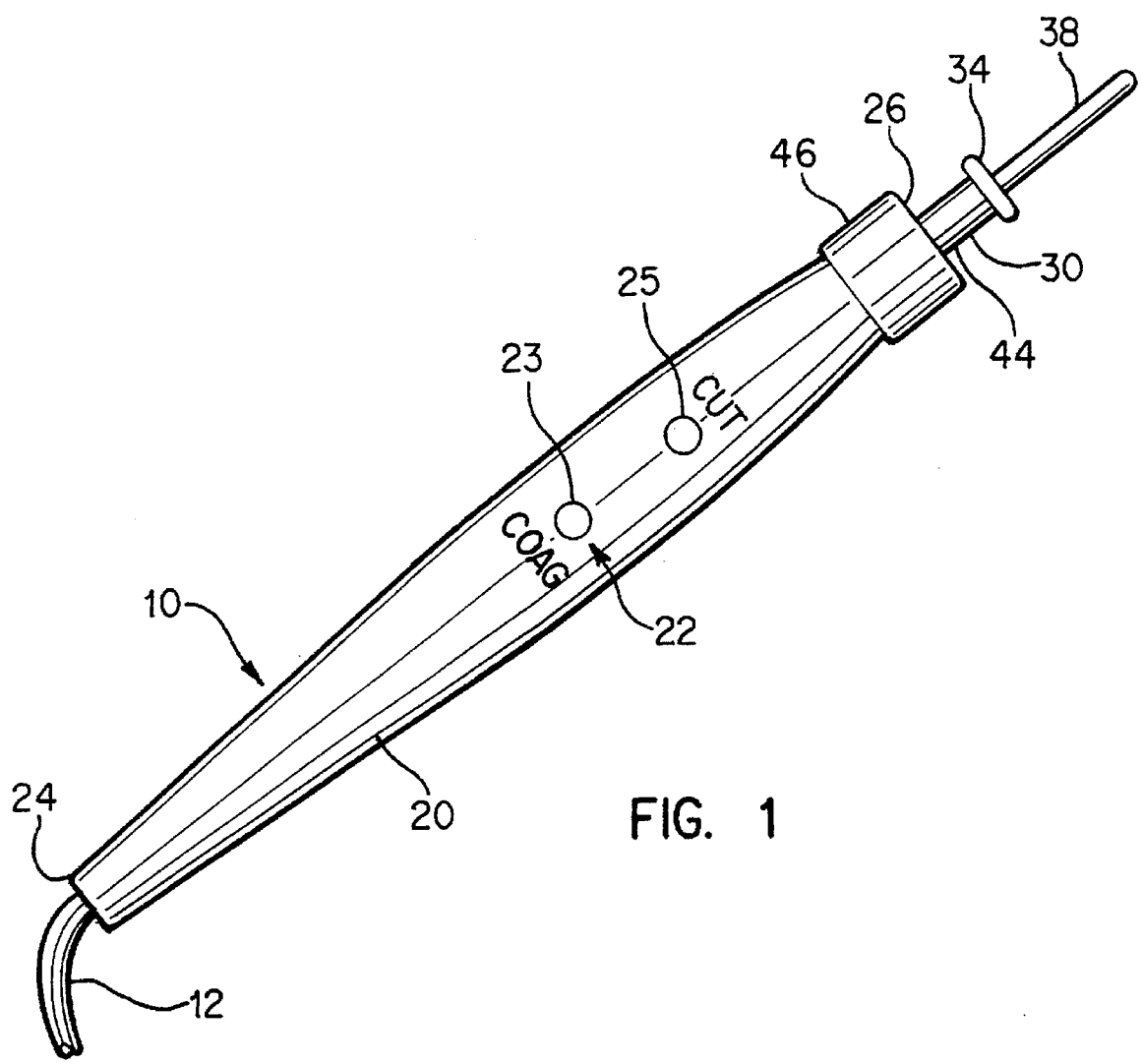
FIG. 1 is a perspective view of an embodiment of the invention, showing the electrode housing slidably positioned in a substantially retracted position.
Figure 4:
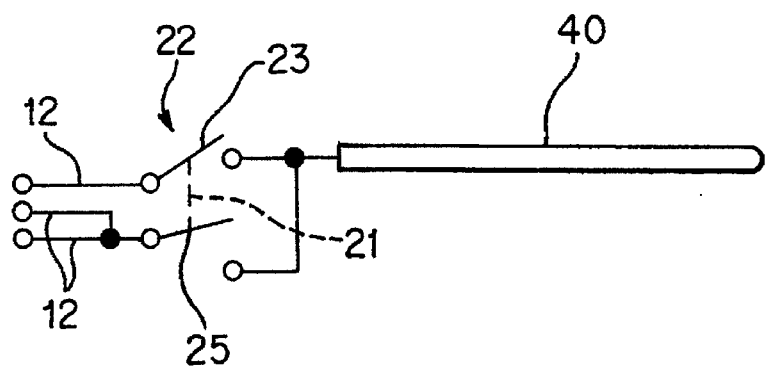
FIG. 4 is a wiring diagram of the electrocautery surgical apparatus, showing first and second actuating means.
Figure 3:
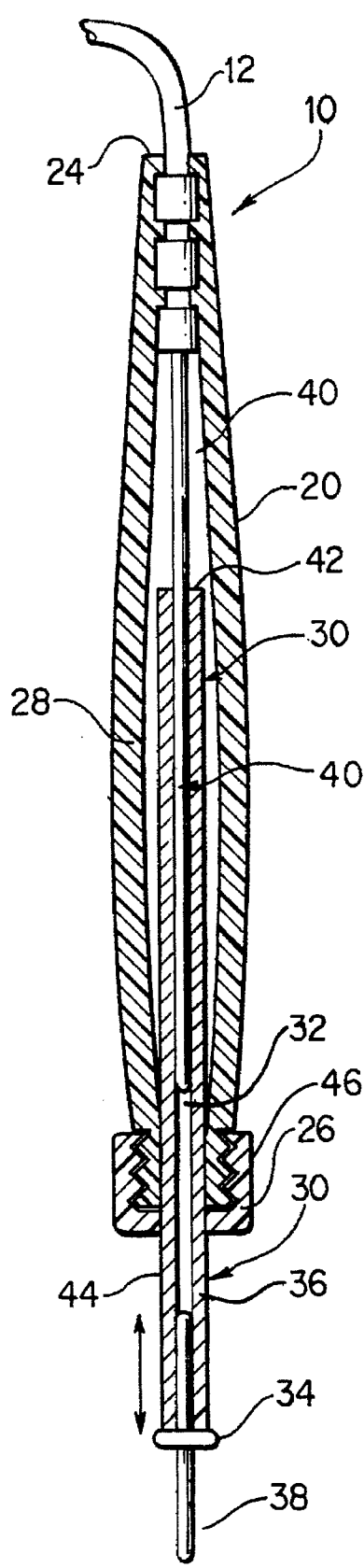
FIG. 3 is a sectional view of the main housing of the embodiment shown in FIG. 1, with the electrode housing slidably positioned in a substantially extended position.
Figure 2:
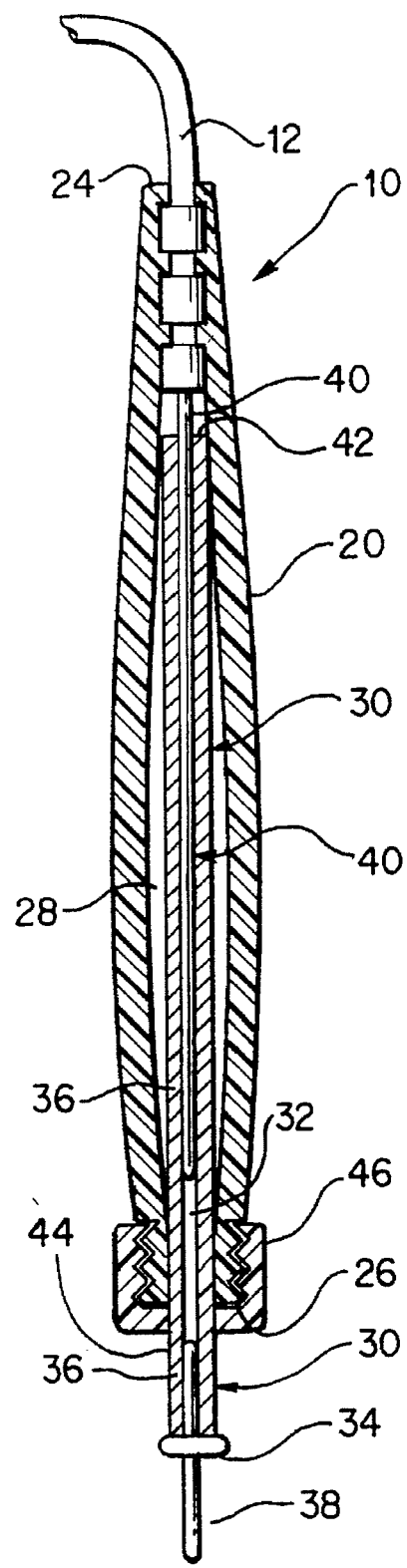
FIG. 2 is a sectional view of the main housing of the embodiment shown in FIG. 1.

As shown in perspective in FIG. 1 and sectionally in FIG. 2 and 3, the manually extendable electrocautery surgical apparatus 10 comprises a non-conductive main housing 20, having at least one actuating means 22 to selectively control electric current received through a suitable electric cord 12 from a remote electrical supply source (not shown). The non-conductive main housing 20 is sized to be comfortably held in a surgeon's hand. The non-conductive main housing 20 comprises a cord end 24 and a distal end 26.

An elongated aperture 28 extends axially within the non-conductive main housing 20 from the distal end 26. The elongated aperture 28 preferably has a circular cross-sectional profile. Alternately, the aperture 28 may be oval, triangular, square, or multiple sided to restrict rotation during use. The elongated aperture 28 is sized to closely receive an electrode housing 30 therein.

The electrode housing 30 has an internal aperture 32 sized to closely receive an electrode 34 therein. The electrode 34 may be disposable or reusable, and is selected from a plurality of commercially available electrodes 34, such as supplied by Valleylab, Inc., Surgical Products Division, Bolder Colo.

Commercially available electrodes 34 include, but are not limited to, a ball electrode for Fulguration/Desiccation; an angled ball electrode for fulguration or desiccation of small tissue areas; a blade electrode for cutting with edge and coagulation with the flat portion of the blade electrode; a needle electrode for precise pin-point cutting and coagulation; a round loop electrode for sectioning of tissue or to obtain tissue samples; and a conization electrode for use in enlarging the cervical aperture or for other tissue removal.

The electrode housing 30 internal aperture 32 preferably extends the length of the electrode housing 30. An electrically conductive material 36 surrounds the internal aperture 32, providing electrical communication between the electrically conductive material 36 and the electrode end 38 of the electrode 34.

An elongated, electrically conductive post 40 is sized to be closely received within the post end 42 of the electrode housing 30. The length of the elongated, electrically conductive post 40 is sized to be longer than the desired extension of the electrode housing 30, and is preferably from one-quarter to one inch longer. The post 40 extends from the main housing 20 to provide electrical communication between the remote electrical current source and the electrically conductive material 36 surrounding the internal aperture 32 within the electrode housing 30.

The electrode housing 30 is coated, or otherwise covered with a non-conductive insulating sleeve 44 to provide an insulating barrier between the electrode housing 30 and the main housing 20. The insulating sleeve 44 further provides insulation about the portion of the electrode housing 30 which slidably extends beyond the main housing 20. This is especially important where the electrode housing 30 is substantially extended for use where deep cuts or cauterizing are required, as shown in FIG. 3.

The electrode housing 30 is slidably received upon the conductive post 40, providing slidably adjustable positioning of the electrode housing 30 in relation to the main housing 20.

A tightening means 46 may be provided at the distal end 26 of the main housing 20, to releasably secure the slidable electrode housing 30 at a desired slidable position in relation to the main housing 20. Any suitable known tightening means 46 may be used, without departing from the scope of this disclosure, or the accompanying claims.

Preferably, the tightening means 46 is a cap threadably received upon the distal end 26 of the main housing 20, which when tightened, compresses the distal end 26 of the main housing 20 against the insulating sleeve 44 of the electrode housing 30, to releasably secure the electrode housing 30 in relation to the main housing 20.

When the tightening means 46 is loosened, the distal end 26 of the main housing is loosened sufficiently to allow the electrode housing 30 to be slidably positioned to a desired extension position in relation to the main housing 20.

Alternately, the electrode housing 30 and the elongated aperture 28 in the main housing 20 may be sized to provide manual slidable adjustment of the electrode housing 30, while providing sufficient resistance to inadvertent slidable adjustment during use.

The actuating means 22 is adapted to selectively control the electric current to provide a current sufficient for selectively cutting a patient's tissue, or to cauterize the patent's tissue, responsive to the needs of the physician. The actuating means 22 may also provide a means to selectively restrict passage of the electrical current from reaching the electrode tip 30.

The actuating means 22 is preferably positioned at an ergonomic location on the main housing 20, for easy access by one of the physician's fingers during use of this apparatus 10. Alternately, the actuating means 22 may be a suitable electrical switch connected to the electrical cord 12 in proximity to the main housing 20. The actuating means 22 may be in the form of a single rocker type switch, or may alternately be in the form of two separate momentary contact switches. Preferably, the actuating means 22 is an internally sealed, water resistant switch.

In use, the manually extendable electrocautery surgical apparatus 10 is connected to a commercially available remote generator (not shown), such as sold byl Valleylab, Inc. Surgical Products Division, Bolder, Colo. The remote generator is in turn connected to a suitable electrical supply means, in preparation for use. The actuating means 22 is turned to an "off" position, and a suitable electrode 34 is inserted into the electrode end 38 of the electrode housing 30. Where the actuating means 22 does not provide an "off" position, the electrocautery surgical apparatus 10 is not connected to the remote electrical supply means until after inserting the electrode 34 into the electrode end 38 of the electrode housing 30.

The electrode housing 30 is then slidably positioned in relation to the main housing 20, and releasably secured therein by tightening the tightening means 46 located at the distal end 26 of the main housing 20. Where no tightening means 46 is used, the electrode housing 30 may be sufficiently closely received within the elongated aperture 28 to allow for manual extension and retraction of the electrode housing 30 within the elongated aperture 28 in the main housing 20, while resisting slidable movement of the electrode housing 30 within the internal aperture 32 during use.

Once the electrode housing 30 is slidably positioned to the desired length in relation to the main housing, the actuating means 22 is actuated to pass current from the remote electrical supply means and the generator, through the electrical cord 12 to the actuating means 22. When the actuating means 22 is in the "on" position, the electric current passes through the electrically conductive post 40 to the electrically conductive material 36 surrounding the internal aperture 32 in the electrode housing 30.

The electrical current passes along the electrically conductive material 36 to the electrode 34 inserted into the electrode end 38 of the electrode housing 30. The current passing into the electrode 34 is used for selectively cutting and for cauterizing a patient's tissue during surgery.

The actuating means 22 may include cauterizing and cutting positions which may be alternately selected by the physician during use. The actuating means 22 may be a single multiple position contact switch 22, with multiple selection positions, such as a rocker switch 21, or may alternately be a first momentary contact switch 23 designed to supply a cauterizing current to the electrode 34, and a second momentary contact switch 25 designed to supply a cutting current to the electrode 34. Where separate actuating means 23, 25 are used, actuation passes current to the electrode 34, while release of the separate actuating means 22 serves to cut off electrical current to the electrode 34.

The insulating sleeve 44 surrounding the electrode housing 30 serves to isolate the electrical current passing through the electrode housing 30 from the non-conductive main housing 20 held by the physician during use. When the electrode housing 30 is extended as shown in FIG. 3, the insulating sleeve 44 surrounding the electrode housing 30 also serves to insulate the exposed side portion of the electrode housing 30 during use.

With this manually extendable electrocautery surgical apparatus 10, the physician may adjustably position the electrode 34 in relation to the main housing 20, without changing the electrode 34. This eliminates the need to change from short to intermediate or long electrodes during the operation, where different operating depths are needed.

The main housing 20 and the electrode housing 30 may be reusable upon sterilization, or may be designed to be sufficiently inexpensive to be disposable after a single use.

Thus, while the present invention has been described in accordance with preferred embodiments thereon, it is to be understood that many alternatives, variations and modifications will be evident to those skilled in this art. Accordingly, the preferred embodiments of this invention, as set forth herein, are intended to be illustrative and not limiting in scope. Various changes may be made without departing from the spirit and scope of this invention, as further defined in the following claims.

What is claimed is:

1. A manually extendable electrocautery surgical apparatus, comprising:
   a) an elongated, non-conductive main housing having a cord end and a distal end, with an elongated aperture extending into the main housing from the distal end;
   b) an elongated electrode housing having an internal aperture extending therethrough, with an electrically conductive material surrounding the internal aperture, and an insulating sleeve surrounding the electrically conductive material, the electrically conductive material surrounding the internal aperture receiving a portion of an electrode therein, and the insulating sleeve sized to be slidably received at least partially within the elongated aperture extending into the main housing from the distal end;
   c) an elongated, electrically conductive post extending within the elongated aperture in the main housing, the post sized to provide electrical contact with the electrically conductive material within the internal aperture of the slidably received, elongated electrode housing; and
   d) an actuating means for selectively actuating an electrical current passing through an electrical cord from remote electrical supply means, through the electrically conductive post to the electrode;
   wherein the elongated electrode housing is slidably positioned in relation to the main housing, to adjustably position the electrode to a desired depth suitable for selectively cauterizing and cutting a patient's tissue during an operation.

2. The manually extendable electrocautery surgical apparatus of claim 1, wherein the actuating means is a first momentary contact switch for passing a cauterizing current to the electrode, and a second momentary contact switch for passing a cutting current to the electrode, and wherein the first and second momentary contact switches are positioned upon the main housing for easy access by the user holding the surgical apparatus.

3. The manually extendable electrocautery surgical apparatus of claim 1, wherein a tightening means is provided upon the distal end of the main housing, to selectively loosen and tighten a portion of the main housing against the electrode housing, to enable the user to selectively extend and retract the electrode housing in relation to the main housing, while restricting movement of the electrode housing in relation to the main housing during use.

4. The manually extendable electrocautery surgical apparatus of claim 3, wherein the tightening means is a cap which is threadably received upon the distal end of the main housing, which when tightened, compresses the distal end of the main housing against the insulating sleeve of the electrode housing, to releasably secure the electrode housing in relation to the main housing.

5. The manually extendable electrocautery surgical apparatus of claim 3, wherein the tightening means is a cap which is threadably received upon the distal end of the main housing, which when tightened, compresses the distal end of the main housing against the insulating sleeve of the electrode housing, to releasably secure the electrode housing in relation to the main housing.

6. The manually extendable electrocautery surgical apparatus of claim 1, wherein the elongated aperture in the main housing is of a circular cross-sectional configuration.

7. The manually extendable electrocautery surgical apparatus of claim 1, wherein the elongated aperture in the main housing is of an oval cross-sectional configuration, to resist rotation of the electrode housing during use.

8. The manually extendable electrocautery surgical apparatus of claim 1, wherein the elongated aperture in the main housing is of a multi-sided cross-sectional configuration, to resist rotation of the electrode housing during use.

9. The manually extendable electrocautery surgical apparatus of claim 1, wherein the electrode housing and the electrode are disposable.

10. A manually extendable electrocautery surgical apparatus, comprising:
    a) an elongated, non-conductive main housing having a cord end and a distal end, with an elongated aperture extending into the main housing from the distal end;
    b) an elongated electrode housing having an internal aperture extending therethrough, with an electrically conductive material surrounding the internal aperture, and an insulating sleeve surrounding the electrically conductive material, the electrically conductive material surrounding the internal aperture receiving a portion of an electrode therein;
    c) an electrically conductive post extending within the elongated aperture in the main housing, the post sized to be slidably received and provide electrical contact with the electrically conductive material within the internal aperture of the elongated electrode housing; and
    d) a first momentary contact switch for passing a cauterizing current to the electrode, and a second momentary contact switch for passing a cutting current to the electrode, the first and second momentary contact switches are positioned upon the main housing for easy access for the user holding the surgical apparatus; and
    wherein the elongated electrode housing is slidably positioned in relation to main housing, to adjustably position the electrode to a desired depth suitable for selectively cauterizing and cutting a patient's tissue during an operation.

11. The manually extendable electrocautery surgical apparatus of claim 10, wherein a tightening means is provided upon the distal end of the main housing, to selectively loosen and tighten a portion of the main housing against the electrode housing, to enable the user to selectively extend and retract the electrode housing in relation to the main housing, while restricting movement of the electrode housing in relation to the main housing during use.

12. The manually extendable electrocautery surgical apparatus of claim 10, wherein the elongated aperture in the main housing is of a circular cross-sectional configuration.

13. The manually extendable electrocautery surgical apparatus of claim 10, wherein the elongated aperture in the main housing is of an oval cross-sectional configuration, to resist rotation of the electrode housing during use.

14. The manually extendable electrocautery surgical apparatus of claim 10, wherein the elongated aperture in the main housing is of a multi-sided cross-sectional configuration, to resist rotation of the electrode housing during use.

15. The manually extendable electrocautery surgical apparatus of claim 10, wherein the tightening means is a cap which is threadably received upon the distal end of the main housing, which when tightened, compresses the distal end of the main housing against the insulating sleeve of the electrode housing, to releasably secure the electrode housing in relation to the main housing.

16. A manually extendable electrocautery surgical apparatus, comprising:
   a) an elongated, non-conductive main housing having a cord end and a distal end, with an elongated aperture extending into the main housing from the distal end;
   b) an elongated electrode housing having an internal aperture extending therethrough, with an electrically conductive material surrounding the internal aperture, and an insulating sleeve surrounding the electrically conductive material, the electrically conductive material surrounding the internal aperture receiving a portion of an electrode therein;
   c) an electrically conductive post extending within the elongated aperture in the main housing, the post sized to be slidably received and provide electrical contact with the electrically conductive material within the internal aperture of the elongated electrode housing; and
   d) an actuating means for selectively actuating an electrical current passing through an electrical cord from a remote electrical supply means to the electrically conductive post;
   e) a tightening means is provided upon the distal end of the main housing, to selectively loosen and tighten a portion of the main housing against the electrode housing, to enable the user to selectively extend and retract the electrode housing in relation to the main housing, while restricting movement of the electrode housing in relation to the main housing during use; and wherein the elongated electrode housing is slidably positioned in relation to main housing, to adjustably position the electrode to a desired depth suitable for selectively cauterizing and cutting a patient's tissue during an operation.

17. The manually extendable electrocautery surgical apparatus of claim 16, wherein the elongated aperture in the main housing is of a circular cross-sectional configuration.

18. The manually extendable electrocautery surgical apparatus of claim 16, wherein the elongated aperture in the main housing is of an oval cross-sectional configuration, to resist rotation of the electrode housing during use.

19. The manually extendable electrocautery surgical apparatus of claim 16 wherein the elongated aperture in the main housing is of a multi-sided cross-sectional configuration, to resist rotation of the electrode housing during use.

20. The manually extendable electrocautery surgical apparatus of claim 16, wherein the electrode housing and the electrode are disposable.

\* \* \* \* \*